United States Patent [19]

Smith

[11] Patent Number: 4,872,876

[45] Date of Patent: Oct. 10, 1989

[54] UNIVERSAL FIT INTRAOCULAR LENS

[75] Inventor: John M. Smith, Santa Barbara, Calif.

[73] Assignee: Nestle S.A., Vevey, Switzerland

[21] Appl. No.: 192,824

[22] Filed: May 11, 1988

[51] Int. Cl.⁴ .............................................. A61F 2/16
[52] U.S. Cl. ......................................................... 623/6
[58] Field of Search ............................................ 623/6

[56] References Cited

U.S. PATENT DOCUMENTS

| | | | |
|---|---|---|---|
| 4,134,160 | 1/1979 | Bayers | 623/6 |
| 4,134,161 | 1/1979 | Bayers | 623/6 |
| 4,254,509 | 3/1981 | Tennant | 623/6 |
| 4,261,065 | 4/1981 | Tennant | 623/6 |
| 4,277,851 | 7/1981 | Choyce | 623/6 |
| 4,296,501 | 10/1981 | Kelman | 623/6 |
| 4,402,579 | 9/1983 | Poler | 623/6 |
| 4,439,873 | 4/1984 | Poler | 623/6 |
| 4,535,488 | 8/1985 | Haddad | 623/6 |
| 4,573,998 | 3/1986 | Mazzocco | 623/6 |
| 4,664,666 | 5/1987 | Barrett | 623/6 |
| 4,673,406 | 6/1987 | Schlegel | 623/6 |

Primary Examiner—Ronald L. Frinks

[57] ABSTRACT

An intraocular lens having a sheet-like support member which can be trimmed by a surgeon to modify the overall diameter of the lens to fit into different sizes of eye chambers. Several sets of support feet are formed on the perimeter of the support member so that the feet at the desired diameter are left untouched by the surgeon's trimming.

9 Claims, 1 Drawing Sheet

U.S. Patent    Oct. 10, 1989    4,872,876
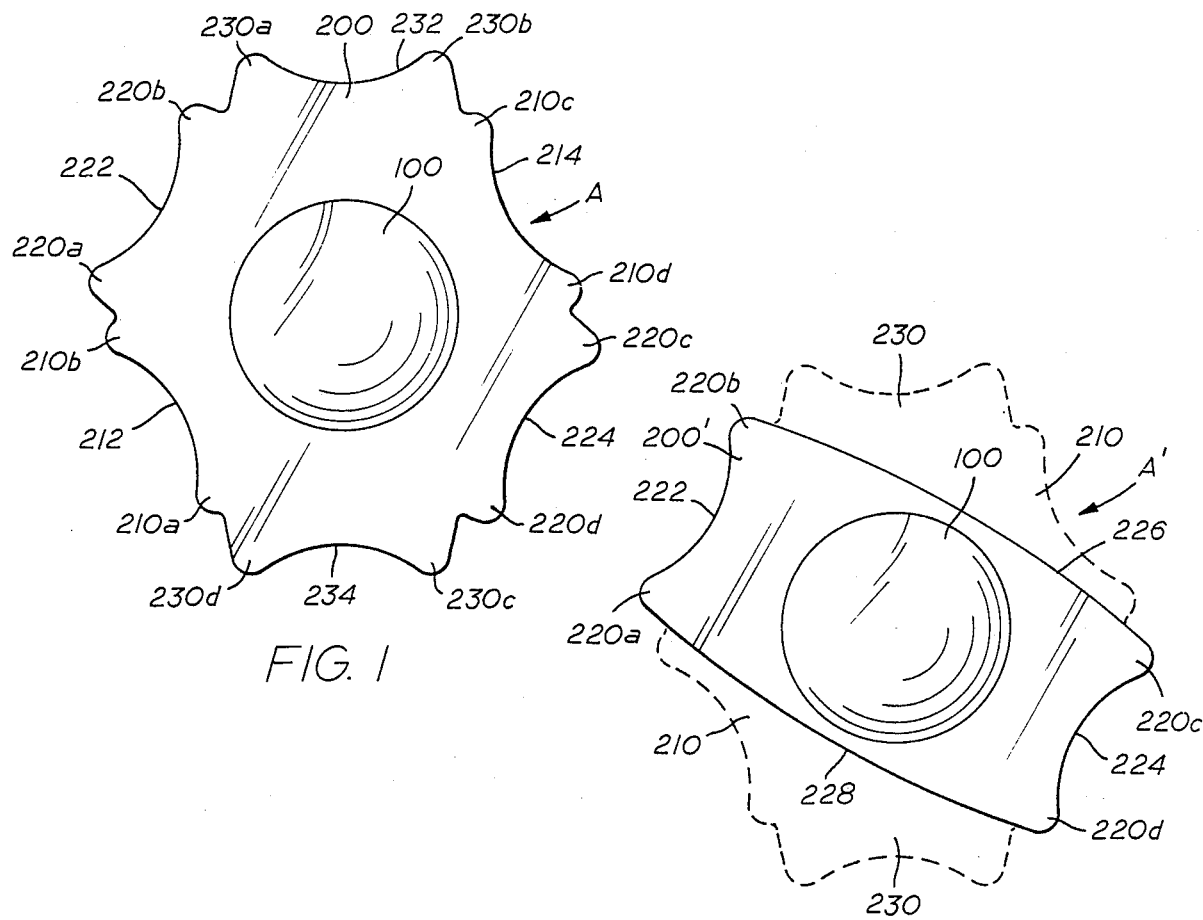
FIG. 1
FIG. 2
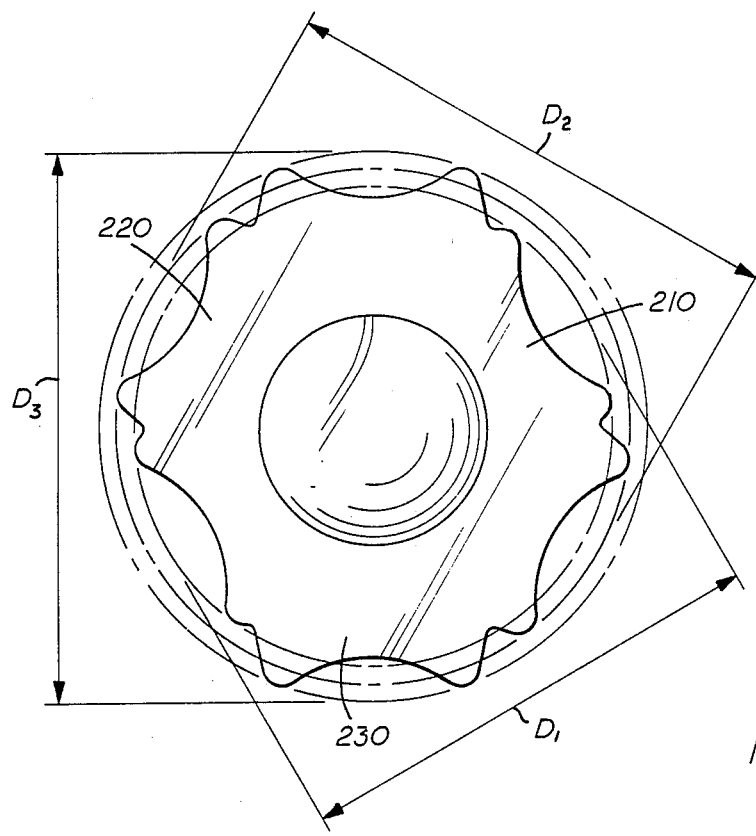
FIG. 3

UNIVERSAL FIT INTRAOCULAR LENS

BACKGROUND OF THE INVENTION

1. Technical Field of the Invention

This invention relates to intraocular lenses (IOLs), which are to be implanted in the eye to replace a natural lens that has been removed because of cataract or other reasons. More particularly, this invention relates to an IOL with an uniquely-shaped haptic designed to be implanted in the anterior or posterior chamber of the eye.

2. Background of the Invention

There are many IOLs of varied shapes on the market, which are used to replace the natural lens of the eye after surgery where the natural lens of the eye is removed. Such lenses include an optical portion and one or more support loops or sheet-like haptics, which retain the IOL optic in the eye in its desired position either in front of the iris in the anterior chamber or to the rear of the iris in the posterior chamber.

The haptics retain the IOL in a relatively fixed position so that light can be focused on the retina. It is advantageous for the haptics to be flexible in order to accommodate changes in shape of the eyeball without causing damage to any of the interior portions of the eye in contact with the haptics.

IOLs can be formed of a single-piece of material such as polymethylmethacrylate (PMMA) where the haptics are formed integral with the optic portion through casting, machining or lathe cutting methods. Other types of IOLs, called multi-piece lenses, can also be formed where haptics made of a material such as polypropylene or PMMA are attached to an optic portion by heat welding or through laser welding, ultrasonic welding or other methods.

More recently, IOLs have been formed of so-called "soft" materials such as hydrogels, acrylics or elastomers. Examples of such materials are described in U.S. Pat. No. 4,573,998. The present invention is particularly adapted for use with IOLs formed of such soft materials.

IOLs are formed with flexible support members or haptics in order to facilitate positioning of the lens in the proper location while accommodating changing shapes of the eyeball. The haptic design, including its flexibility, is considered to be important in achieving maximum patient comfort and lack of postoperative complications, ease of implantation and effectiveness of maintaining the lens in its proper position.

The haptics or IOLs formed of the so-called "soft" materials have haptics that are sheet-like or substantially flat, which are formed integral with the lens optic. It is important that the haptics are sized so that they fit accurately and snugly into the eye of the patient. Typically, a surgeon must have available a large inventory of lenses wit haptics of different sizes so that he can accurately fit the lens to the particular eye on which he is working. This is an expensive requirement. It would be beneficial to have a single lens which could fit any size opening in order to obviate the requirement for a large inventory of surgically clean lenses.

Attempts have been made to provide one lens which has adjustable haptics so that a single lens can be used to fit a wide range of eye openings. One such attempt is illustrated in U.S. Pat. No. 4,134,161. This lens has a stationary haptic having two toes on one side of the lens while the other side of the lens has an adjustable haptic having two toes. The adjustable haptic can be moved in or out with respect to the optic portion of the lens, thereby adjusting the overall outside dimension, measured from toe to toe, of the lens. Adjustment is achieved by providing ridges and grooves on the adjustable haptic which mate with ridges and grooves on a stationery portion of the lens. Once the desired adjustment is made, the adjustable haptic is held n position by means of clamps which force the mating ridges and grooves together. This arrangement requires that manufacture of the lens include formation of relatively intricate moving parts having small interlocking features. Some of the parts having smaller cross-sections, such as the clamps, are subject to breakage either during installation or after a period of use.

Another attempt at making an adjustable lens can be seen in U.S. Pat. No. 4,296,501. This lens has an L-shaped stationary haptic on one side of the optic portion while the other haptic on the other side of the optic portion is formed of two connected arms, the second of which can pivot about its connection with the first arm. By means of pivoting the second arm, the surgeon can adjust the overall outside dimension of the haptics, from toe to toe, to the desired dimension for the eye being worked on. Once the second arm is in the desired position, it can be sutured in place by means of holes provided in both arms. This lens, again, requires somewhat complex manufacturing procedures to provide a lens having relatively intricate interlocking parts which can move with respect to one another. The mating of the rotating arms of the second haptic is achieved by reducing the thickness of these arms. The sections of reduced thickness are held in the desired orientation by attachment means such as suturing at a small number of attachment points, such as the holes provided. In order for this adjustable haptic to be sufficiently rigid to hold the lens in place, the attaching together of the pivoting arms must be tight and permanent. The pivot point, therefore, being of reduced thickness and utilizing only a few attachment points, is the weakest portion of the haptic structure. Any fatigue of the sutures or plastic parts will result in breakage or at least loosening of the attachment between the pivoting arm and the stationary arm. This will result in a loose haptic which will allow the lens to become dislodged.

SUMMARY OF THE INVENTION

The present invention is a one piece soft material lens capable of fitting several different diameter eye openings. The haptics are formed so that the surgeon can choose the size required at the time of surgery and trim from the haptics the portions not required for the desired size.

BRIEF DESCRIPTION OF THE DRAWINGS

FIG. 1 is a plan view of the lens of the present invention.

FIG. 2 is a plan view of the lens of FIG. 1 after the unwanted haptic portions have been trimmed away.

FIG. 3 is a plan view of the lens of FIG. 1 demonstrating the three different haptic diameters typically available.

DETAILED DESCRIPTION OF THE INVENTION

Referring to FIG. 1, an intraocular lens A includes an optic portion 100 and a haptic portion 200. The haptic portion 200 has three sets of protuberances 210, 220, and 230 on its perimeter. Each set of protuberances 210, 220 and 230 is formed of four protuberances arranged in pairs, with each individual protuberance being substantially equidistant from the center of the optic portion 100. For example, the protuberance set 210 has individual protuberances 210a, b, c, and d with protuberances 210a and 210b forming one pair and protuberances 210c and 210d forming another pair. These two pairs are equidistant from and arranged on opposite sides of the optic portion 100.

As seen in FIG. 1, the protuberance set 210 constitutes the set of protuberances closest to the center of the optic portion 100. The next most distant set of protuberances is designated by reference numeral, 220 which is composed of individual protuberances 220a, b, c and d. These again are arranged in pairs which are equidistant and on opposite sides of the optic portion 100. The most distant set of protuberances is designated by reference numeral 230, which is formed of individual protuberances 230a, b, c and d, arranged in equidistant pairs similar to the other sets.

The protuberances 210a and 210b are connected by an uninterrupted arc 212 which has its center of curvature outside the haptic portion 200. Similarly, the protuberances 210c and 210d are connected by an uninterrupted arc 214, which also has its center of curvature outside haptic portion 200. The protuberances 220a and 220b, in similar fashion, are connected by an arc 222 and the protuberances 220c and 220d by the arc 224. Finally, the protuberances 230a and 230b are connected by an arc 232 and the protuberances 230c and 230d, by an arc 234.

A line bisecting arcs 212 and 214 intersects a line bisecting arcs 222 and 224 at about a 60° angle. Similarly the two aforementioned lines intersect a line bisecting the arcs 232 and 234 at 60° angles. This angular orientation could be modified as required if the number of sets of protuberances were changed for a different embodiment.

For example, if only two sets of protuberances were desired, the intersecting angle would likely be approximately 90°. In any given set of protuberances such as those designated by reference numeral 210 each pair of protuberances 210a and 210b, for example, are connected by an unbroken arc 212 with no other protuberances between them. This is important to insure that once the unwanted portions of haptic 200 are trimmed away, there will be no rough edges remaining on any portion of the haptic which might contact eye tissue.

Preferably the IOL A is formed of an optically transparent medical grade soft pliant material such as silicone, butyl acrylate, polymethane, or hydrogel. The IOL is preferably molded with a round hatic and then the protuberances can be formed by use of a stamp or other cutting mechanism. Alternatively, the lens and haptic can be molded with the protuberances in place. It would also be possible to mold the entire lens with a round haptic portion formed of an hydrophylic material, then machine the protuberance features into the haptic portion and finally hydrate the material.

FIG. 2 shows a lens A' as it appears after the unwanted portions of the haptic have been trimmed away. The optic portion 100 is mounted in an eye by means of the remaining haptic portion 200'. The protuberances 220a, b, c, and d remain and constitute the contact points between the haptic and the structure of the eye.

When the surgeon determines the required haptic diameter according to the diameter of the eye opening, in this particular case choosing the diameter of protuberance set 220, he or she cuts along lines 226 and 228. This removes from the lens haptic portions containing the unnecessary parts of the protuberance sets 210 and 230.

Cut lines 226 and 228 are shown as arcs having a very large radius of curvature extending between the protuberances 220b, 220c, and 220a, 220d; however, these cut lines can be modified by the surgeon during the operation as he sees fit according to such variables as the condition of the eye tissue and the size of incision being used.

Once placed in the eye opening, the protuberances 220a, b, c, and d contact the eye structure to hold the lens in place. It can be seen that the ends of the remaining haptics formed of the protuberances 220a, b, c, and d and the intermediate arcs 222 and 224 are part of the original perimeter of the haptic portion as manufactured. This insures that they retain a smooth unbroken edge achieved during the manufacturing process. The edges cut by the surgeon, here being the arcs 226 and 228, need not be as smooth since they will have no contact with the eye structure. This insures that irritation and damage of surrounding eye tissue is minimized.

It can be seen that if the surgeon wants to use a smaller diameter haptic, he would trim away the haptic portion leaving the protuberance set 210, or if he or she wants a larger diameter haptic, he or she would trim away the haptic portion leaving the the protuberance set 230. The protuberance contours shown here are for illustration purposes only. Any contours desired can be used without departing from the present invention.

FIG. 3 illustrates a lens of the present invention having three protuberance sets, 210, 220 and 230, which are molded to provide three typical diameters $D_1$, $D_2$, and $D_3$. By way of illustration in a typical lens, the diameter $D_1$ of a circle which contains the outermost points of the protuberances of set 210 would be 12.0 millimeters. Similarly, the diameter $D_2$ of the circle containing the outermost points of the protuberances of set 220, being the intermediate set, would be 13.0 millimeters and diameter $D_3$ of a circle containing the outermost points of the protuberances of the largest set, 230, would be 14.0 millimeters.

In the lens chosen for illustration, the arcs 212, 222, 232, 214, 224, and 234 would have radii of curvature of 3.7 millimeters. All the protuberances would have radii of curvature of 0.25 millimeter and the angular separation relative to the center of the lens between two protuberances of a given pair would vary between approximately 22 degrees and approximately 27 degrees.

Various modifications and improvements to the present invention will become apparent to those with ordinary skill in the art. All such modifications or improvements are considered to be included within the scope of the invention as defined by the appended claims.

I claim:

1. An intraocular lens for use in eyes of different sizes, comprising:
   an optic;
   a haptic which is connected to and projects outwardly from at least a portion of the optic; the haptic including an outer periphery with a plurality of support portions adapted to maintain and support the optic within an eye, the support portions being located on one of a plurality of different diameters of different length relative to the optic, so that the support portions along one diameter can be selected and the other support portions removed for adapting the lens to fit in an eye of a predetermined size.

2. The lens of claim 1, wherein:

the haptic includes a substantially flat sheet lying in a plane perpendicular to the focal axis of the optic; and the support portions are protuberances on the perimeter of the sheet.

3. The lens of claim 2, wherein:

the protuberances are arranged in sets;

each set has at least one protuberance on the opposite side of the optic from at least one of the other protuberances in that set; and all protuberances in one set are equidistant from the focal axis of the optic.

4. The lens of claim 3, wherein:

each set of protuberances is located at a distance from the focal axis of the optic different from the distance from the focal axis of the optic of any other set of protuberances; and each set of protuberances has an angular location with respect to the plane of the optic which is different from the angular location of any other set of protuberances.

5. The lens of claim wherein each set of protuberances includes two groups of protuberances located on opposite sides of the optic from each other.

6. The lens of claim 5, wherein each group includes a pair of protuberances.

7. The lens of claim 6, wherein the optic and the haptic are formed integrally from a single piece of material.

8. The lens of claim 7, wherein the material is a soft, pliant material.

9. An intraocular lens which can be trimmed to fit a plurality of different sizes of ocular chambers, comprising:

an optic portion;

a substantially flat sheet support haptic surrounding and attached to the optic portion;

support feet formed on the perimeter of the support haptic, wherein:

the support feet are arranged in groups;

each group includes support feet equidistant from the center of the optic portion;

each group is at a different distance from the center of the optic portion from the other groups; and the groups are arranged in angular locations so that the support haptic can be trimmed to remove therefrom all unnecessary groups, leaving undisturbed only the group having the desired distance from the center of the optic portion.

* * * * *